United States Patent
Johnson et al.

(10) Patent No.: US 8,420,801 B2
(45) Date of Patent: Apr. 16, 2013

(54) RECOVERY OF NUCLEIC ACIDS FROM MAGNETIC GLASS PARTICLES

(75) Inventors: Jenny A. Johnson, Castro Valley, CA (US); Erich Kyger, Antioch, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 607 days.

(21) Appl. No.: 12/684,762

(22) Filed: Jan. 8, 2010

(65) Prior Publication Data
US 2011/0172408 A1 Jul. 14, 2011

(51) Int. Cl.
*C07H 21/00* (2006.01)

(52) U.S. Cl.
USPC ...................................... 536/25.42

(58) Field of Classification Search .................. None
See application file for complete search history.

(56) References Cited

U.S. PATENT DOCUMENTS

| | | | |
|---|---|---|---|
| 5,185,243 A * | 2/1993 | Ullman et al. | 435/6.12 |
| 5,573,907 A * | 11/1996 | Carrino et al. | 435/6.18 |
| 5,679,524 A * | 10/1997 | Nikiforov et al. | 435/6.11 |
| 6,255,477 B1 | 7/2001 | Kleiber et al. | |
| 6,534,262 B1 | 3/2003 | McKernan et al. | |
| 6,548,256 B2 | 4/2003 | Lienau et al. | |
| 6,870,047 B2 | 3/2005 | Kleiber et al. | |
| 8,026,068 B2 * | 9/2011 | Pinsl-Ober et al. | 435/6.12 |
| 2006/0003357 A1 | 1/2006 | McKernan et al. | |

FOREIGN PATENT DOCUMENTS

| | | |
|---|---|---|
| EP | 1577389 A2 | 9/2005 |
| EP | 1577389 A3 | 11/2005 |
| EP | 1577389 B1 | 7/2007 |
| EP | 1983051 A2 | 10/2008 |
| EP | 1983051 A3 | 12/2008 |
| EP | 2157181 A1 | 2/2010 |
| WO | 9958644 A1 | 11/1999 |
| WO | 2004013155 A2 | 2/2004 |
| WO | 2004013155 A3 | 2/2004 |
| WO | 2004042058 A2 | 5/2004 |
| WO | 2004042058 A3 | 5/2004 |
| WO | 2008119488 A1 | 10/2008 |
| WO | 2011000013 | 4/2011 |

OTHER PUBLICATIONS

Iralu, Jonathan V., et al., 1993, "Diagnosis of *Mycobacterium avium* Bacteremia by Polymerase Chain Reaction", Journal of Clinical Microbiology, 31(7):1811-1814.

Neonakis, Ioannis K., et al., 2008, "Molecular diagnostic tools in mycobacteriology", Journal of Microbiological Methods, 75:1-11.

Shamputa, I. C., et al., 2004, "Molecular genetic methods for diagnosis and antibiotic resistance detection of mycobacteria from clinical specimens", AMPIS, 112:728-752.

* cited by examiner

*Primary Examiner* — Lawrence E Crane
(74) *Attorney, Agent, or Firm* — Olga Kay

(57) ABSTRACT

The present invention is a method of separating nucleic acids using a solid phase capable of binding nucleic acids, such as magnetic glass particles, where binding of nucleic acids to the solid phase is enhanced by the presence of an ethylene-amine compound. The invention further includes a reaction mixture for isolating nucleic acids containing an ethylene-amine compound and kits for carrying out the method.

14 Claims, No Drawings

RECOVERY OF NUCLEIC ACIDS FROM MAGNETIC GLASS PARTICLES

FIELD OF THE INVENTION

The invention relates to the field of isolating nucleic acids and specifically, to the field of isolating nucleic acids using solid supports.

BACKGROUND OF THE INVENTION

Isolation of nucleic acids is an important step in molecular diagnostics. The quality and quantity of nucleic acids isolated from a sample greatly affects the success of downstream diagnostic applications. The clinical and field applications also demand that the isolation procedure be quick and amenable to automation.

Many procedures exist for isolating nucleic acids from various organisms and tissues. Some types of clinical and environmental samples present special challenges to successful isolation of nucleic acids. For example, certain tissues such as bone contain large amount of extracellular material that require removal before nucleic acids can be accessed. Some organisms, such as fungi, plants and bacteria possess cell walls or outer membranes that require harsh chemical treatment. The reagents used in the harsh treatments pose challenges for the downstream applications that utilize the isolated nucleic acids. Furthermore, degradation of the target nucleic acids during harsh treatment may lead to a false-negative result in the downstream detection assay. Yet to be clinically acceptable, a diagnostic procedure must have sufficient sensitivity, i.e. avoid false-negative results in patients' samples. Therefore in the field of molecular diagnostics, there is a need for improvement of the methods of isolating nucleic acids in order to make the diagnostic procedures sensitive, reliable and easy to perform.

A prerequisite for successful nucleic-acid based diagnostic test is isolation of undegraded, inhibitor-free nucleic acids. At the same time, there is a demand for simple, automation-friendly nucleic acid isolation procedures. Recently it has become popular to isolate nucleic acids using solid supports, such as for example, spherical microparticles. Especially popular are magnetic microparticles containing or coated with a glass-like substance, commonly referred to as "Magnetic Glass Particles" or "MGPs." The nucleic acids isolation procedures employing MGPs require comparatively few steps and are easily automated. Especially popular are MGPs made by the sol-gel method, described in European publication EP 1 154 443 or U.S. Pat. Nos. 6,255,477 and 6,870,047.

The general descriptions and specific examples of MGPs made by the sol-gel method are readily available in the literature (see e.g. EP 1 154 443). These MGPs consist of a ferromagnetic core coated with silica-based glass-like material. The ferromagnetic core typically contains iron oxides, e.g. $Fe_3O_4$ or $Fe_2O_3$. The core may be a simple iron core, or may be made of a composite material. The core can also consist of a crystalline, ceramic or glass-like structure in which iron oxide is embedded. The glass coating may consist of amorphous material containing silicon oxide and further may contain one or more additional metal oxides such as boron oxide ($B_2O_3$), aluminum oxide ($Al_2O_3$), calcium oxide (CaO), barium oxide (BaO), potassium oxide ($K_2O$), sodium oxide ($Na_2O$), magnesium oxide (MgO) or lead oxide ($Pb_2O_3$). In some embodiments, the glass is silicon oxide and also contains one or more compounds in the following concentration range: $B_2O_3$ (0-30%), $Al_2O_3$ (0-20%), CaO (0-20%), BaO (0-10%), $K_2O$ (0-20%), $Na_2O$ (0-20%), MgO (0-18%), $Pb_2O_3$ (0-15%). The glass may also contain a smaller percentage (0-5%) of a number of other oxides such as $Mn_2O_3$, $TiO_2$, $As_2O_3$, $Fe_2O_3$, CuO and CoO. Surfaces made of a composition of borosilicate glass have proven to be especially effective. Borosilicate glasses have a boron oxide content of more than 25%, e.g. a 70/30 composition of $SiO_2/B_2O_3$.

The magnetic particles are sometimes modified with functional groups that facilitate the binding of nucleic acids. Such groups include, without limitation, poly-T oligonucleotides, for the capture of poly-A-containing nucleic acids, streptavidin, for the capture of biotin-labeled nucleic acids and specific probe sequences for the capture of nucleic acids containing the unique sequence complementary to the probe. However, most universally useful are magnetic particles with unmodified surfaces that are capable of isolating any nucleic acid present in the sample, regardless of the sequence.

A typical nucleic acid isolation protocol using MGPs commences with disruption of the cells or tissues in order to release the nucleic acids. The commonly used tissue disruption procedures are of chemical, enzymatic or physical nature, including ultrasound, high pressure, shear forces, strong bases, detergents or chaotropic agents, proteases or lipases. For chemical and enzymatic lysis, the lysis reagent typically includes a buffering agent, a salt, one or more of a denaturing substance and a chaotropic substance, a protease and optionally, a nuclease inhibitor and a preservative. The lysis reagent causes digestion of proteins, inhibition of nucleases, and solubilization of lipids, lipoproteins, and the like. For example, the buffering agent may be Tris, the salt may be a sodium, a potassium, an ammonium or a magnesium salt, such as a chloride or an acetate, the detergent may be sodium dodecyl sulfate, Triton-X or Tween, the chaotropic reagent may be urea, thio-urea, sodium iodite, sodium dodecyl sulfate, sodium perchlorate, guanidinium thiocyanate, guanidinium isothiocyanate or guanidinium hydrochlorite, the nuclease inhibitor may be a chelator such as EDTA, the preservative may be a metal azide, and the protease may be proteinase K. Typically, the sample is incubated with the lysis reagent at temperatures between 70 and 100° C., e.g., 90-95° C.

For most samples, the lysis reagents and conditions described above are sufficient to achieve the lysis of the cells and release nucleic acids into solution. Unfortunately, for some types of samples, lysis poses a major challenge. Some cells, organisms and tissues require harsh lysis conditions in order to break up the cell wall or tissue and release cellular contents. For example, Gram-positive pathogens such as *Mycobacterium tuberculosis* have lipid-rich peptidoglycan cell walls. There is a world-wide need for rapid methods of detecting *M. tuberculosis* and other mycobacteria. However, nucleic acid isolation is often a limiting factor for reaching desirable levels of assay sensitivity. See Neonakis et al. (2008) Molecular diagnostic tools in mycobacteriology, *J. Microbiol. Methods,* 75:111. Currently the desired sensitivity in a mycobacteria detection assay is achieved with a multi-step nucleic acid isolation procedure that includes repeated wash and centrifugation steps. See Shamputa et al. (2004) Molecular genetic methods for diagnosis and antibiotic resistance detection of mycobacteria from clinical specimens, *APMIS,* 122:728. Such procedure however is not automatable and not practical for most users.

In a typical method of isolating nucleic acids using MGPs, after the cellular compartments in the sample have been broken up to release the nucleic acids, the sample is brought into contact with MGPs in order to achieve binding of the nucleic acids to the MGPs. The MGPs may be added to the sample prior to lysis. For example, MGPs can be present in the vessel to which the initial sample is added. It has been found that the presence of MGPs does not affect lysis of the sample. Alternatively, the sample may be lysed first and MGPs introduced only after the lysis step is complete.

To achieve binding to MGPs, the sample is typically mixed with MGPs and incubated in this binding mixture for a period of time sufficient for the binding to occur. This step can be easily optimized by determining the quantity of immobilized nucleic acids on the surface of the magnetic glass particles at different points in time or by determining the yield of nucleic acids following different incubation times. Generally, incubation times of between 10 seconds and 30 minutes are appropriate for nucleic acids.

In most instances, the lysis reagent containing released nucleic acids is a suitable environment for the binding to MGPs to occur. However, in some instances, the lysis reagent makes the environment unsuitable for the binding of nucleic acids to the surface of magnetic glass particles. Especially where magnetic glass particles have unmodified surface, the binding between nucleic acids and the surface of the particles is dependent on conditions such as pH and ionic strength of the binding mixture. It has been found that maximum binding of nucleic acids to MGPs occurs at low pH, such as pH 5 or lower. However, for some applications, such low pH of the binding mixture may not be achieved. For example, the lysis reagent for lysing mycobacteria has a pH value of 12 or higher. In a typical procedure for isolating mycobacterial nucleic acids, the pH is lowered during a neutralization step following cell lysis but to not less than pH 9. At pH 9 or higher, the binding of nucleic acids to magnetic glass particles is inefficient. Up to the present time, this inefficiency of binding has been overcome by prolonged incubation times. This way of solving the problem is impractical for clinical applications. Furthermore, prolonged incubation threatens stability of the nucleic acid templates especially RNA templates.

SUMMARY OF THE INVENTION

The present invention is a method of separating nucleic acids from a sample solution containing nucleic acids, comprising contacting the sample solution with a solid phase capable of binding nucleic acids and a binding mixture comprising an ethylene-amine compound; incubating the sample solution containing the solid phase under the conditions in which the nucleic acids may bind to the solid phase; and separating the solid phase from the solution. The method optionally includes a step of washing the bound nucleic acids prior to elution. In some embodiments, the method includes detecting the nucleic acids after isolation. The invention further includes a reaction mixture for isolating nucleic acids, the mixture containing a solid phase capable of binding nucleic acids and an ethylene-amine compound. The invention also includes a kit for separating nucleic acids from a sample using solid phase the kit comprising: a solid phase capable of binding nucleic acids and an ethylene-amine compound.

DETAILED DESCRIPTION OF THE INVENTION

Definitions

As used herein, the term "ethylene-amine compound" refers to a molecule having a general formula $H_2N-(CH_2-CH_2-NH)_n-CH_2-CH_2-NH_2$, wherein n is 0-9 or more. Ethylene-amine compounds useful in the present invention include, but are not limited to, ethylene-diamine (EDA), diethylene-triamine (DETA), triethylene-tetramine (TETA), tetraethylene-pentamine (TEPA) and pentaethylene-hexamine (PEHA). One of skill in the art will appreciate that other ethylene-amine compounds are useful in the present invention.

As used herein, the term "sample" refers to a mixture or solution containing the substance of interest, e.g. a nucleic acid. The sample may comprise a solid or liquid tissue, a body fluid, a culture or suspension of eukaryotic cells (including plant, fungal, animal or human cells), a culture or suspension of prokaryotic cells (including bacterial cells). The sample may comprise viruses. The sample may also comprise a cell-free solution containing a substance of interest. Depending on the nature of the sample, it may require chemical or physical treatment to facilitate isolation of the substance of interest from the sample. For example, the sample may require treatment to release nucleic acids from cellular and subcellular compartments.

As used herein, the term "component" of a biological sample refers to a class of molecules (e.g., proteins, nucleic acids, etc.) or a specific target such as a specific protein or nucleic acid sequence that one wishes to detect.

As used herein, the term "nucleic acid" refers to polymers of deoxyribonucleotides (containing 2-deoxy-D-ribose) (i.e., DNA), polyribonucleotides (containing D-ribose) (i.e., RNA), and any other N-glycoside analogs of a purine or pyrimidine base, or modified purine or pyrimidine bases, or a combination thereof.

In the method of the present invention, the nucleic acids are isolated from a sample using magnetic glass particles, wherein the binding of the nucleic acids to the magnetic glass particles is enhanced by the presence of one or more ethylene-amine compounds.

In some embodiments, the sample contains whole cells. The cells are lysed using a lysis reagent suitable for disrupting the cellular membranes and, if present, cell walls in order to release the nucleic acids from the cellular and subcellular compartments. Various methods of disputing cells and tissues are known in the art. Many methods are referenced and described in Sambrook & Russell, *Molecular Cloning, A Laboratory Manual* (3rd Ed, 2001)).

In some embodiments, the sample contains Gram-positive bacteria. The Gram-positive bacteria are lysed using a lysis reagent comprising a strong chemical base (e.g. alkali hydroxide), a detergent and a salt and having pH greater than 12. In some embodiments, the sample containing Gram-positive bacteria is heated to between 80° C. and 100° C., usually about 95° C. and incubated for between 5 and 30 minutes, usually about 15 minutes.

According to the present invention, the sample containing nucleic acids free from cellular and subcellular compartments is brought in contact with magnetic glass particles under conditions suitable for the binding of nucleic acids to the magnetic glass particles. It has been discovered that the addition of ethylene-amine compounds to the binding mixture greatly increases the efficiency of binding of nucleic acids to the surface of magnetic glass particles. This phenomenon is especially beneficial at high pH. The efficiency of binding is further increased by the presence of metal salts, for example, magnesium or manganese salts, such as chloride or acetate salts, in the binding mixture.

In some embodiments, the concentration of ethylene-amine compounds is between 10 and 65 mM, e.g., 16 mM.

Following the binding step, the magnetic glass particles with bound nucleic acids can be separated from the solution containing ethylene-amine compounds. Depending on the size and type of magnetic glass particles, the particles either separate out of the fluid during the incubation period, or remain in suspension after the incubation and require further separation. If a separation step is required, the particles with bound nucleic acids are separated from the sample solution by application of a magnetic field. For instance, the magnetic glass particles can be pulled to the wall or the bottom of the sample vessel in which the incubation was performed. The liquid containing any unbound substances and contaminants present in the sample can then be removed from the sample vessel via pipetting or aspiration.

The magnetic glass particles with bound nucleic acids may optionally be washed one or more times with one or more wash solutions. A wash solution has a composition that does not cause the nucleic acids to be released from the particle surface, but that washes away the undesired contaminants still associated with the nucleic acids or magnetic glass particles. In some embodiments, the initial wash solution contains alcohol, for example ethanol or isopropanol. The wash solution may also contain a chaotropic salt and a buffer. In some embodiments, the subsequent wash solution is alcohol-free, but contains a salt, a buffer and optionally, a preservative. This wash step may take place by incubating the wash solution with magnetic glass particles to which nucleic acids are bound. The particles may be resuspended during this step to achieve maximum contact with the washing fluid. The contaminated wash solution is then removed from the sample vessel.

After the last wash step, the magnetic glass particles with bound nucleic acids may be dried briefly in a vacuum, or the residual wash fluid may be allowed to evaporate. If desired, nucleic acids can be separated from the magnetic particles and optionally removed from the vessel containing the magnetic particles, leaving the particles behind. Nucleic acids may be eluted from the magnetic glass particles using a buffer having a low salt content. In some embodiments, the elution buffer contains Tris. Optionally, the elution buffer may contain preservatives and nuclease inhibitors, for example chelators such as EDTA. In other embodiments, the elution buffer is water with or without preservatives.

In some embodiments, nucleic acids may remain bound to the magnetic particles during downstream applications. (See e.g. U.S. Application Publication No. 20040014070). In other embodiments, nucleic acids are dislodged from the magnetic glass particles, but the particles remain in the vessel with nucleic acids for downstream applications. For example, the publication U.S.20040014070 teaches that magnetic glass particles made by the sol-gel method improve the efficiency of amplification of nucleic aids by PCR. In other instances, the nucleic acids may be separated from the magnetic glass particles after elution. Typically, the solution containing nucleic acids is removed from the vessel containing the magnetic glass particles.

In some embodiments, the method of isolation of nucleic acids further includes amplification and detection of the isolated target nucleic acids. For example, the amplification and detection are performed using PCR, see *Principles and Applications for DNA Amplification* (ed. H. A. Erlich, Freeman Press, New York, N.Y., 1992); *PCR Protocols: A Guide to Methods and Applications* (eds. Innis, et al., Academic Press, San Diego, Calif., 1990). The amplification and detection may also be performed via the ligase chain reaction (LCR) (U.S. Pat. Nos. 5,185,243, 5,679,524 and 5,573,907) or any other suitable nucleic acid amplification technology. While any downstream analysis method is compatible with the isolation method of the present invention, the composition of the lysis solution and the binding solution according to the present invention are especially compatible with the downstream PCR application.

In a real-time PCR assay, the signal generated by the labeled probe is proportional to the amount of input target nucleic acid. The greater the input, the earlier the fluorescence signal crosses a predetermined threshold value ($C_t$). Therefore one can determine relative or absolute amounts of the target nucleic acid by comparing the samples to each other or to a control sample with a known amount of nucleic acid.

In another embodiment, the invention is a reaction mixture for isolating nucleic acids. The reaction mixture may contain a lysis reagent, the reagent comprising one or more detergents, an ethylene-amine compound and optionally, a metal salt such as, for example, a magnesium or a manganese salt, one or more preservatives, and/or one or more chelators. In some embodiments, the lysis reagent has a pH value of 12 or more. In some embodiments, the lysis reagent in the reaction mixture comprises one or more detergents at a concentration of 1-10%, one or more chelators such as EDTA at a concentration of 0.5-2 mM, one or more preservatives, such as sodium azide at a concentration of 0.01-0.1%, an ethylene-amine compound at a concentration of 10-65 mM and a metal salt, such as magnesium or manganese salt, such as a chloride or an acetate at a concentration of 5-25 mM.

In some embodiments, the reaction mixture further contains a sample including nucleic acids to be isolated. In some instances, the sample contains lysed Gram-positive bacteria as the source of nucleic acid. In yet other embodiments, the reaction mixture contains magnetic glass particles. In some instances the particles are manufactured by the sol-gel method described in the U.S. Pat. No. 6,870,047 and references cited therein.

In yet another embodiment, the invention is a kit for isolating nucleic acids using magnetic glass particles. The kit includes a lysis reagent, the reagent comprising one or more detergents, and optionally, one or more preservatives, an ethylene-amine compound and optionally a magnesium or manganese salt. In some embodiments, the lysis reagent, the ethylene-amine compound and the magnesium or manganese salt are provided in separate containers. In some embodiments, the lysis reagent may have a pH value of 12 or more. In some embodiments, the lysis reagent included in the kit comprises one or more detergents at a concentration between 1-10%, one or more chelators such as EDTA at a concentration between 0.5-2 mM, one or more preservatives, such as sodium azide at a concentration between 0.01-0.1%, an ethylene-amine compound at a concentration between 10-65 mM and a magnesium or manganese salt, such as magnesium chloride or manganese acetate at a concentration between 5-25 mM. The kit may further include magnetic glass particles. Magnetic glass particles may be incorporated into a lysis reagent or present in a separate container in the kit. When magnetic glass particles are present in a separate vessel, the particles may be suspended in alcohol such as isopropanol. In some instances, the magnetic particles included in the kit of the present invention are manufactured by the sol-gel method described in the U.S. Pat. No. 6,870,047 and references cited therein. In some embodiments the kit optionally includes a neutralization reagent, a wash reagent and an elution reagent. The neutralization reagent may contain a buffer, a salt and a preservative and have a pH between 6 and 8, most preferably pH 7.5. In some embodiments, the buffer may be Tris, the salt may be magnesium chloride and the preservative may be sodium azide. The wash reagent may contain alcohol. The elution reagent may contain a buffer and a preservative and have a pH of 8.5.

EXAMPLES

As an illustration only and not to limit the scope of the invention, the method was applied to isolation of nucleic acids from *Mycobacterium tuberculosis* (MTB).

Example 1

For lysis, the sample comprising 100 µL of a *Mycobacterium tuberculosis* (MTB) cell suspension or the same volume of MTB DNA in 67 mM phosphate pH 6.8 was combined with 400 µL of lysis reagent (50 mM NaOH, 1% Triton X-100, 1 mM EDTA, 0.05% $NaN_3$, pH 12+) and incubated for 15 minutes at 95° C. Then 400 µL of neutralization reagent was added (8-64 mM ethylene-amine, 200 mM Tris, 8-23 mM $MgCl_2$ or $Mg(OAc)_2$ 0.05% $NaN_3$, pH 7.5). Then 100 uL of magnetic glass particles (Roche Molecular Systems, Inc., Branchburg, N.J.) were added and the sample incubated for 5-30 min at room temperature or at 37° C. The magnetic glass particles were then separated by removing the supernatant, and washed twice with 7.5 mM sodium citrate dihydrate, 0.05% (w/v) MIT, pH 4.1. The nucleic acids were eluted with 50-100 µL elution reagent (30 mM Tris, pH 8.5, 0.2% w/v methyl-4-hydroxybenzoate (methyl paraben), 0.09% $NaN_3$). The post-lysis procedures were performed either manually or automatically by the Hamilton Star instrument (Hamilton Robotics, Inc., Reno, Nev.).

The isolated nucleic acid was tested by quantitative PCR also known as real-time PCR. The PCR was performed with 50 µL of eluate and 50 µL of master mix comprising 154 mM Tricine, 110 mM potassium hydroxide, 190 mM potassium acetate, 19% glycerol (v/v), 2.3% DMSO, 1.16 mM dATP, 1.16 mM dCTP, 1.16 mM dGTP, 1.16 mM dUTP, upstream and downstream primer, target probe, internal control probe, DNA polymerase, uracil-N-DNA glycosylase, 0.09% sodium azide (w/v), pH 8.50, and 20 copies/reaction of internal control DNA. The amplification conditions on the COBAS® TAQMAN® 48 Analyzer were: 5 min at 50° C. followed by two cycles of 98° C. for 20 sec, 61° C. sec, and 70° C. sec, then 55 cycles of 95° C. for 25 sec, 61° C. for 40 sec, and 70° C. for 20 sec.

The results are expressed as the "cycles-to-threshold" ($C_t$) value (a cycle number at which the fluorescence from a sample exceeds the background fluorescence and thus "crosses the threshold"). $C_t$ is reflective of the starting amount of the nucleic acid template. A lower Ct value indicates a greater starting amount of the nucleic acid template in the reaction, while a higher $C_t$ value indicates a lower starting amount of the nucleic acid template in the reaction. Tables 1-3 show $C_t$ values for each PCR reaction containing nucleic acids isolated using the method of the present invention.

TABLE 1

Nucleic acid recovery from whole MTB aided by an ethylene-amine and a metal salt

|  | Ct | Std Dev (n = 2) |
|---|---|---|
| [TETA*] mM | | |
| 8 | 37.0 | 1.24 |
| 16 | 36.4 | 0.55 |
| 32 | 36.1 | 0.42 |
| 64 | 37.0 | 0.05 |
| [TETA] mM/[$MgCl_2$]mM | | |
| 0.0 | 38.8 | 0.35 |
| 8.10 | 36.6 | 0.22 |
| 16.15 | 36.3 | 0.12 |
| 32.15 | 36.7 | 0.61 |

*TETA—Triethylenetetramine

TABLE 2

Nucleic acid recovery from whole MTB aided by various ethylene-amines and a metal salt

| | | RT Binding | | 37° C. Binding | |
|---|---|---|---|---|---|
| No. | Additives | Ct | Std Dev (n = 3) | Ct | Std Dev (n = 3) |
| 1 | 8 mM $MgCl_2$ | 29.70 | 0.05 | 29.42 | 0.12 |
| 2 | 8 mM $MgCl_2$ + 16 mM EDA* | 30.16 | 0.33 | 29.65 | 0.05 |
| 3 | 8 mM $MgCl_2$ + 16 mM DETA | 29.02 | 0.05 | 28.96 | 0.17 |
| 4 | 8 mM $MgCl_2$ + 16 mM TETA | 28.61 | 0.03 | 28.28 | 0.17 |
| 5 | 8 mM $MgCl_2$ + 16 mM TEPA | 28.37 | 0.19 | 28.29 | 0.09 |
| 6 | 8 mM $MgCl_2$ + 16 mM PEHA | 31.46 | 0.30 | 31.57 | 0.30 |
| 1 | 23 mM $MgCl_2$ | 30.62 | 0.23 | 31.11 | 0.40 |
| 2 | 23 mM $MgCl_2$ + 16 mM EDA | 30.30 | 0.27 | 30.40 | 0.31 |
| 3 | 23 mM $MgCl_2$ + 16 mM DETA | 28.47 | 0.06 | 28.77 | 0.22 |
| 4 | 23 mM $MgCl_2$ + 16 mM TETA | 28.33 | 0.19 | 28.31 | 0.41 |
| 5 | 23 mM $MgCl_2$ + 16 mM TEPA | 28.57 | 0.14 | 28.59 | 0.10 |
| 6 | 23 mM $MgCl_2$ + 16 mM PEHA | 31.78 | 1.10 | 29.96 | 0.59 |

*EDA—Ethylenediamine;
DETA—Diethylenetriamine;
TETA—Triethylenetetramine;
TEPA—Tetraethylenepentamine;
PEHA—Pentaethylenehexamine

TABLE 3

Nucleic acid recovery from whole MTB aided by an ethylene-amine and various metal salts

| No. | Additives | Ct | Std Dev (n = 3) |
|---|---|---|---|
| 1 | None | 36.74 | 0.52 |
| 2 | 8 mM $MgCl_2$ | 30.78 | 0.41 |
| 3 | 16 mM TETA | 28.22 | 0.05 |
| 4 | 8 mM $Mg(OAC)_2$ + 16 mM TETA* | 28.45 | 0.26 |
| 5 | 23 mM $Mg(OAC)_2$ + 16 mM TETA | 28.78 | 0.29 |
| 6 | 8 mM $Mn(OAC)_2$ + 16 mM TETA | 31.07 | 0.15 |
| 7 | 23 mM $Mn(OAC)_2$ + 16 mM TETA | 32.65 | 0.11 |
| 1 | None | 34.73 | 0.36 |
| 2 | 8 mM $MgCl_2$ | 27.17 | 0.20 |
| 3 | 16 mM TEPA | 31.50 | 0.80 |
| 4 | 8 mM $Mg(OAC)_2$ + 16 mM TEPA | 26.95 | 0.23 |
| 5 | 23 mM $Mg(OAC)_2$ + 16 mM TEPA | 26.82 | 0.27 |
| 6 | 8 mM $Mn(OAC)_2$ + 16 mM TEPA | 26.85 | 0.44 |
| 7 | 23 mM $Mn(OAC)_2$ + 16 mM TEPA | 30.50 | 0.65 |

*TETA—Triethylenetetramine

TABLE 4

Cell-free MTB nucleic acid recovery aided by an ethylene-amine and metal salts

| No. | Additives | Ct | Std Dev (n = 3) |
|---|---|---|---|
| 1 | None | 42.86 | 0.55 |
| 2 | 8 mM $MgCl_2$ | 35.38 | 0.22 |
| 3 | 16 mM TEPA* | 39.10 | 3.77 |
| 4 | 8 mM $Mg(OAC)_2$ + 16 mM TEPA | 35.57 | 0.63 |
| 5 | 23 mM $Mg(OAC)_2$ + 16 mM TEPA | 35.52 | 0.58 |
| 6 | 8 mM $Mn(OAC)_2$ + 16 mM TEPA | 35.78 | 0.32 |

TABLE 4-continued

Cell-free MTB nucleic acid recovery aided by an ethylene-amine and metal salts

| No. | Additives | Ct | Std Dev (n = 3) |
|---|---|---|---|
| 7 | 23 mM Mn(OAC)$_2$ + 16 mM TEPA | 39.70 | 0.76 |
| 1 | None | 42.99 | 1.33 |
| 2 | 8 mM MgCl$_2$ | 35.15 | 0.12 |
| 3 | 23 mM MgCl$_2$ | 35.78 | 0.72 |
| 4 | 8 mM Mg(OAC)$_2$ | 35.46 | 0.20 |
| 5 | 23 mM Mg(OAC)$_2$ | 37.17 | 0.48 |
| 6 | 16 mM TETA | 35.15 | 0.19 |
| 7 | 8 mM MgCl$_2$ + 16 mM TETA | 34.68 | 0.14 |
| 8 | 23 mM MgCl$_2$ + 16 mM TETA | 34.47 | 0.19 |
| 9 | 8 mM Mg(OAC)$_2$ + 16 mM TETA | 34.66 | 0.29 |
| 10 | 23 mM Mg(OAC)$_2$ + 16 mM TETA | 34.65 | 0.38 |

*TETA—Triethylenetetramine

The results demonstrate that the ethylene-amine compounds improve the recovery of nucleic acids using solid supports such as magnetic glass particles. The improvement is further enhanced by the presence of metal salts, for example, magnesium or manganese salts, such as chloride or acetate salts.

While the invention has been described in detail with reference to specific examples, it will be apparent to one skilled in the art that various modifications can be made within the scope of this invention. Thus the scope of the invention should not be limited by the examples described herein, but by the claims presented below.

We claim:

1. A method of separating nucleic acids from a sample solution containing nucleic acids, comprising
   a. contacting the sample solution with a solid phase capable of binding nucleic acids the solid phase comprising particles having a magnetic core and a silica-containing outer layer and a binding mixture comprising ethylene-diamine or higher order oligomeric relatives thereof;
   b. incubating the sample solution containing the solid phase under the conditions in which the nucleic acids bind to the solid phase; and
   c. separating the solid phase from the solution.

2. The method of claim 1, further comprising washing the solid-phase-bound nucleic acids.

3. The method of claim 1, further comprising eluting nucleic acids from the solid phase.

4. The method of claim 1, further comprising lysis of cells present in the sample solution prior to step (a).

5. The method of claim 4, wherein said sample solution is obtained by the lysis of Gram-positive bacteria selected from a group consisting of *Bacillus, Clostridium, Staphylococcus, Streptococcus, Enterococcus, Mycobacterium*, and combinations thereof.

6. The method of claim 1, wherein the binding mixture in step a further comprises magnesium or manganese ions.

7. The method of claim 1 wherein the binding mixture in step a further comprises a hydroxide of an alkali metal and a detergent.

8. The method of claim 7 wherein the binding mixture in step a comprises a mixture of equal volumes of Solution 1 (50 mM NaOH, 1% Triton X-100, 1 mM EDTA, 0.05% NaN$_3$, pH 12+) and Solution 2 (10-65 mM ethylene-amine, 200 mM Tris, 5-25 mM MgCl$_2$, 0.05% NaN$_3$, pH 7.5).

9. A reagent mixture for separating nucleic acids from a sample by contacting the sample with a solid phase, the mixture comprising: a solid phase comprising particles having a magnetic core and a silica-containing outer layer and ethylene-diamine or higher order oligomeric relatives thereof.

10. The reaction reagent mixture of claim 9 further comprising a hydroxide of an alkali metal and a detergent.

11. The reagent mixture of claim 9 further comprising magnesium or manganese ions.

12. A kit for separating nucleic acids from a sample by contacting the sample with a solid phase, the kit comprising: a solid phase capable of binding nucleic acids, the solid phase comprising particles having a magnetic core and a silica-containing outer layer and ethylene-diamine or higher order oligomeric relatives thereof.

13. The kit of claim 12, further comprising one or more of a lysis reagent, a neutralization reagent, a wash reagent and an elution reagent.

14. The kit of claim 12, wherein the lysis reagent contains a hydroxide of an alkali metal and a detergent, a neutralization reagent contains an ethylene-diamine or higher order oligomeric relatives thereof, magnesium or manganese ions and a buffer.

* * * * *